United States Patent
Gruber

(10) Patent No.: US 10,285,933 B2
(45) Date of Patent: May 14, 2019

(54) PERSONAL CARE COMPOSITION CONTAINING OZONE-STRESSED YEAST LYSATES

(71) Applicant: ARCH PERSONAL CARE PRODUCTS, L.P., Alpharetta, GA (US)

(72) Inventor: James Vincent Gruber, Washington, NJ (US)

(73) Assignee: ARCH PERSONAL CARE PRODUCTS L.P., Alpharetta, GA (US)

( * ) Notice: Subject to any disclaimer, the term of this patent is extended or adjusted under 35 U.S.C. 154(b) by 177 days.

(21) Appl. No.: 15/236,355

(22) Filed: Aug. 12, 2016

(65) Prior Publication Data

US 2016/0346195 A1   Dec. 1, 2016

Related U.S. Application Data

(63) Continuation of application No. 11/248,522, filed on Oct. 12, 2005, now abandoned.

(60) Provisional application No. 60/618,698, filed on Oct. 13, 2004.

(51) Int. Cl.
| | |
|---|---|
| A61K 8/14 | (2006.01) |
| A61K 8/55 | (2006.01) |
| C12N 1/06 | (2006.01) |
| A61K 8/99 | (2017.01) |
| A61Q 19/08 | (2006.01) |
| A61K 8/73 | (2006.01) |
| A61Q 19/00 | (2006.01) |

(52) U.S. Cl.
CPC .............. *A61K 8/99* (2013.01); *A61K 8/14* (2013.01); *A61K 8/553* (2013.01); *A61K 8/73* (2013.01); *A61Q 19/00* (2013.01); *A61Q 19/08* (2013.01); *C12N 1/063* (2013.01); *A61K 2800/522* (2013.01); *A61K 2800/524* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 2,239,345 | A | 4/1941 | Sperti |
| 4,540,571 | A | 9/1985 | Schimanski |
| 5,019,391 | A | 5/1991 | Bunte et al. |
| 5,057,320 | A | 10/1991 | Evans et al. |
| 5,514,591 | A | 5/1996 | Levin |
| 5,643,587 | A | 7/1997 | Scancarella et al. |
| 5,650,140 | A | 7/1997 | Bergmann et al. |
| 5,676,956 | A | 10/1997 | Duffy et al. |
| 5,776,441 | A | 7/1998 | Scancarella et al. |
| 6,103,246 | A | 8/2000 | Tisdale et al. |
| 6,461,857 | B1 | 10/2002 | Scholz et al. |
| 2003/0215407 | A1 | 11/2003 | Klein |
| 2003/0232091 | A1* | 12/2003 | Shefer .................. A61K 8/671 424/490 |

FOREIGN PATENT DOCUMENTS

| | | |
|---|---|---|
| EP | 1108419 | 6/2001 |
| EP | 1514537 | 3/2005 |
| JP | 60215609 | 10/1985 |
| JP | 4248968 | 9/1992 |
| JP | 2001333784 | 12/2001 |
| JP | 2004519208 | 7/2004 |
| WO | 0059462 | 10/2000 |
| WO | 0202075 | 1/2002 |
| WO | 03068161 | 8/2003 |
| WO | 2004075621 | 9/2004 |

OTHER PUBLICATIONS

Theiele, JJ., et al., "In-Vivo Exposure to Ozone Depletes Vitamins C and E and Induces Lipid Peroxidation in Layers of Murine Skin" Free Rad. Biol. Med. 23, 385-391 (1997). Epidermal.

Cotovio, J., et al., "Generation of oxidative stress in human cutaneous models following in vitro ozone exposure," 15, 357-362 (2001).

Weber, Su., et al., "High-Pressure Liquid Chromatography Analysis of Ozone-Induced Depletion of Hydrophilic and Lipophilic Antioxidants in Murine Skin," Method Enzy., 319, 536-546 (2000).

Hinze, H., et al., "Effect of ozone on ATP, cytosolic enzymes and permeability of *Saccharamyces* cerevisiae," Arch Microbiol 147, 105-108 (1987).

(Continued)

*Primary Examiner* — Irene Marx
(74) *Attorney, Agent, or Firm* — McBee Moore Woodward & Vanik IP, LLC

(57) ABSTRACT

A personal care composition includes an ozone-stressed yeast lysate; and a preservative, in which the preservative is selected from phenoxyethanol, isopropyl alcohol, benzyl alcohol, propylene glycol, butylene glycol, pentylene glycol, methylparaben, propylparaben, butylparaben, benzalkonium chloride, Quaternium 15, methylisothiazolinone, methylchloroisothiazolinone, DMDM hydantoin, imidazolidinyl urea, diazolidinyl urea, butylated hydroxytoluene, tocopherol, triclosan, chlorohexidine digluconate, and combinations thereof, and the ozone-stressed yeast lysate is produced by a method including exposing growing yeast to ozone by aerating the yeast for a time period of between five minutes and seventy-two hours with an aeration gas having an ozone concentration of from 0.0001 millimolar (mM) to 1.0 millimolar (mM) based on the total volume of the fermentation broth to produce ozone-stressed yeast lysing the ozone-stressed yeast to produce an ozone-stressed yeast lysate comprising water-soluble and water-insoluble components; and separating the water-soluble components from the water-insoluble components to produce an ozone-stressed yeast lysate containing the water-soluble components.

13 Claims, 1 Drawing Sheet

(56) References Cited

OTHER PUBLICATIONS

Collinson, et al., "Inducibility of the response of yeast cells to peroxide stress," Journal of General Microbiology. 138, 329-335 (1992).

Dubeau H et al., "Genetic effects of ozone—Introduction of point mutation and genetic recombination in *Saccharomyces* cerevisiae" Mutation Research/Genetic Toxicology, vol. 102, No. 3, 1982, pp. 249-259.

* cited by examiner

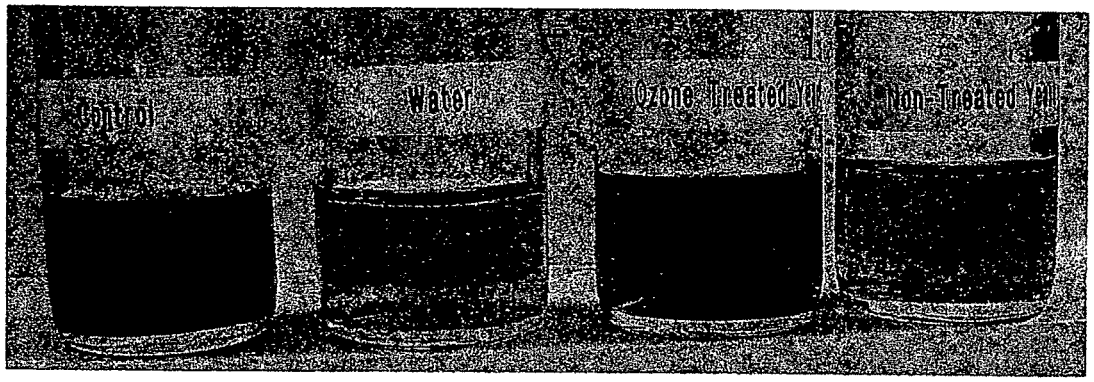

PERSONAL CARE COMPOSITION CONTAINING OZONE-STRESSED YEAST LYSATES

CROSS-REFERENCES TO RELATED APPLICATIONS

This is a continuation application of application Ser. No. 11/248,522 (now abandoned), filed on Oct. 12, 2005, which claims priority of Provisional Application No. 60/618,698, filed on Oct. 13, 2004. This application claims the priorities and benefits of all these prior applications and incorporates these prior applications by reference in their entireties.

FIELD OF THE INVENTION

This invention relates generally to personal care compositions, and more specifically to such compositions containing ozone-stressed yeast lysates.

BACKGROUND OF THE INVENTION

Ozone is increasingly becoming recognized as a detrimental agent for skin cells. Ozone can affect lipids, proteins, nucleic acids and sugars but is especially severe to key antioxidants located in skin cells. The damage appears to be most severe at the surface layers of skin, and diminishes as one probes into deeper dermal and epidermal layers. Ozone, which is generated by a number of natural sources such as lightning, is also generated by various industrial sources, such as the burning of fossil fuels, and in particular, the emission from automobiles, which are a leading cause of urban smog. Ozone is formed when reactive oxygen radicals combine with oxygen gas to form a molecule that contains three moles of oxygen as can be seen in the empirical equation:

$$O_2 + O \rightarrow O_3$$

In particular, it is now generally recognized that ozone will diminish the amounts of vitamins C and E in the upper layers of the stratum corneum as well as oxidize key lipids in the bi-layer of the stratum corneum. In addition, ozone has been implicated in protein and nucleic acid damage as well. Thiele, J. et al., "In-Vivo Exposure to Ozone Depletes Vitamins C and E and Induces Lipid Peroxidation in Epidermal Layers of Murine Skin" *Free Rad. Biol. Med.* 23, 385-391 (1997). Vitamins C and E are key natural antioxidants that offer important defense mechanisms against the ravages of ozone to the deeper layers of the skin. The lipid bi-layer is the most important physical barrier between the interior of the human body and external elements. Deterioration of the lipid bi-layer increases trans-epidermal water loss and leads to drying and cracking of the skin. Methods to measure the effects of ozone stress on human skin and human skin-mimics are disclosed in Cotovio, J. et al., "Generation of oxidative stress in human cutaneous models following in-vitro ozone exposure," 15, 357-362 (2001) and Weber, S U. et al., "High-Performance Liquid Chromatography Analysis of Ozone-Induced Depletion of Hydrophilic and Lipophilic Antioxidants in Murine Skin," *Method Enzy.*, 319, 536-546 (2000). In addition, melanin is a key photoprotective pigment located in the skin and hair that has not previously been shown to be a target for ozone degradation. Other key cutaneous lipids that ozone can attack include cholesterol, cholesterol esters, free fatty acids and ceramides that make up the lipid bilayers of the skin.

Damage to nucleic acids can lead to cellular mutations and apoptosis of important skin cells. Such skin cells include, but are not limited to fibroblasts, keratinocytes, dermal papilla, melanocytes, macrophages, corneocytes, Langerhan cells, neutrophils, adipocytes, sebocytes, and nerve cells which reside at the surface of the skin. Likewise, ozone can deteriorate proteins and sugars that comprise the extracellular matrix and natural moisturizers in the skin.

The use of cosmetic products to protect the human body, and in particular the skin, from the damaging effects of ozone is known. For example, Japanese patent JP60215609, published October 1985, discloses the use of melanoidins to protect the skin against ozone. European patent EP1108419, published June 2000, discloses the use of combinations of hesperetin and curcumin derivatives in topical applications to protect the skin. International Patent Application WO0059462, published October 2000, discloses the use of combinations of oxidoreductases and proteinase inhibitors to protect the skin against the damage caused by increased ozone concentrations in the atmosphere. Likewise, International Patent Application WO0202075, published January 2002, discloses the use of creatine and creatine derivatives as a prophylaxis for the symptoms of ozone induced skin lesions and inflammatory or degenerative skin conditions.

In a similar fashion to human skin cells, yeast respond to the presence of ozone. High concentration of ozone is typically lethal to yeast. However, it has been suggested that lower concentrations of ozone may not only be nonlethal, but may also influence the yeast to increase production of certain proteins, including glyceraldehyde-3-phosphate dehydrogenase (GAPDH). GAPDH is a key "housekeeper" enzyme that is responsible for oxidatively converting glyceraldehyde-3-phosphate into 1,3-diphosphoglycerate in human skin as part of the glucose cellular enzymatic pathways. It is known that the enzymatic activity of GAPDH is affected by oxidative stress and ultraviolet light. Hinze, H et al., "Effect of ozone on ATP, cytosolic enzymes and permeability of *Saccharomyces cerevisiae*," *Arch Microbiol.* 147, 105-108 1987.

The use of yeast and derivatives thereof has become quite popular in topical cosmetic and therapeutic applications. For example, active yeast lysates have been sold in the personal care industry for many years. Historically, these products have been marketed and sold as activators of tissue oxygen uptake. It has been found that stressed yeast lysates will stimulate growing cells to increase their oxygen consumption. Additionally, it has been discovered that yeast tissue respiratory factors could also stimulate collagen production in skin.

For example, U.S. Pat. No. 2,239,345, issued April, 1941, discloses a method for improving the uptake of oxygen in living yeast cells by application of components derived from yeast. U.S. Pat. No. 5,057,320, issued October, 1991, discloses yeast compositions containing picolinic acid to increase oxygen uptake in living mammalian skin cells. Additionally, U.S. Pat. No. 5,514,591, issued May, 1996, discloses improved methods to measure the ability of yeast extracts to stimulate oxygen uptake in human skin cells. Despite previous attempts to increase oxygen uptake in human skin cells, there is no solution that directly addresses the need of ozone protection for the skin.

Therefore, what is needed in the art is a product that provides ozone protection to skin cells and skin cell components which include, but are not limited to nucleic acids, the extracellular matrix proteins, vitamin reservoirs, and the like.

It has been surprisingly found that *Saccharomyces cerevisiae*, more commonly known as Baker's Yeast, respond well to growth stresses, such as heat shock, ozone, peroxides and ultraviolet light. Surprisingly, the stress provides enhanced production of stress response agents, or protective cell components in the yeast. These stress response agents have therapeutic effects on human skin cells.

SUMMARY OF THE INVENTION

One aspect of the invention relates to an ozone-stressed yeast lysate produced by a method including the steps of: exposing growing yeast to an ozone concentration sufficient to produce ozone-stressed yeast; lysing the ozone-stressed yeast to produce an ozone-stressed yeast lysate comprising water-soluble and water-insoluble components; and separating the water-soluble components from the water-insoluble components to produce an ozone-stressed yeast lysate comprising the water-soluble components.

Another aspect of the invention relates to a personal care composition including: an ozone-stressed yeast lysate and a preservative, wherein the preservative is selected from the group consisting of alcohol, glycol, parabens, hydantoins, quaternary nitrogen-containing compounds, isothiazolinones, aldehyde-releasing agents, halogenated compounds, and combinations thereof.

A further aspect of the invention relates to a composition for topical treatment of skin, including the ozone-stressed yeast lysate described above and a cosmetically acceptable vehicle for application to the skin.

Yet another aspect of the present invention relates to a method for preparing a personal care composition including an ozone-stressed yeast lysate effective in reducing or minimizing ozone-induced skin degradation when applied to skin cells. The method includes the steps of: growing yeast in a fermentation broth; exposing the yeast to ozone by aerating the yeast for a time period of between about five minutes and about seventy-two hours with an aeration gas having an ozone concentration of from about 0.0001 millimole (mM) to about 1.0 millimole (mM) based on the total volume of the fermentation broth to produce ozone-stressed yeast; lysing the ozone-stressed yeast to produce an ozone-stressed yeast lysate; and incorporating the ozone-stressed yeast lysate into a personal care composition.

BRIEF DESCRIPTION OF THE FIGURES

FIG. 1 is a color photograph of the results from ozone exposure to water, non-ozone-stressed yeast lysate and ozone treated yeast lysate using an ozone reactive dye as an indicator of ozone degradation.

DETAILED DESCRIPTION OF THE INVENTION

The ozone-stressed yeast lysate of the present invention is obtained through standard fermentation processes known to those skilled in the art. As defined for the purposes of this invention, a yeast lysate is a composition derived from yeast grown on a nutritional growth media that is subsequently killed in such as way as to afford a product that includes cellular yeast components including, but not limited to, the nutrient broth, cellular protein material, cellular nuclear material, cellular cytoplasmic material, cellular protoplasmic material and/or cell wall components. Typically, the yeast lysate is essentially water-soluble. For purposes of this disclosure, water-soluble means 0.1 gram of yeast components that are dissolved in 1 gram of water. As defined for the purposes of this invention, an ozone-stressed yeast is a yeast that has undergone exposure to ozone, otherwise referred to as "ozone treatment". An ozone-stressed yeast lysate is a lysate of the ozone-stressed yeast. As used herein, the term "yeast" is meant to encompass a single yeast cell, multiple yeast cells, and/or a culture of yeast cells.

The yeast of the present invention can be of various genus known to those skilled in the art including, but not limited to: *Arthroascus, Aureobasidium, Botryoascus, Brettanomyces, Candida, Citeromyces, Clavispora, Cryptococcus, Debaryomyces, Dekkera, Filobasidium, Guilliermondella, Hansenula, Haneseniaspora, Hormoascus, Klockera, Kluyveromyces, Leucosporidium, Lipomyces, Malassezia, Metschnikowia, Nadsonia, Nematospora, Oosporidium, Pachysolen, Pachytichospora, Penicillium, Pichia, Prototheca, Rhodosporidium, Rhodotorula, Saccharomyces, Saccharomycodes, Saccharomycopsis, Schizosaccharomyce, Schwanniomyces, Sporobolomyces, Sporopachydermia, Tremella, Trichosporan, Trigonopsis, Torulaspora, Torulopsis, Williopsis, Yarrowia, Zygosaccharomyces*. Preferably, the yeast is from the genus *Saccharomyces*. Typically the yeast is *Saccharomyces cerevisiae*, also known as Baker's yeast.

The yeast is grown on growth media which has peptone and other common growth media ingredients. An example of preferred growth media called "yeast fermentation media," can be found in the "Handbook of Microbiological Media," published by CRC Press.

Methods for growing yeast are known to those skilled in the art. Generally speaking, the yeast can be grown simply in an open-air fermentation vessel, or by using a sealed biological fermentor, available from New Brunswick Scientific, Edison, N.J.

Commercially available ozone generators used for the ozone treatment of the yeast can be found at, for example, Erwin Sander Elektroapparatebau GmbH, Uetze-Eltze, Germany. Preferably, the ozonizer Model IV from Sander is used. In most circumstances, an ozone detector is used in addition to the ozone generator. Suitable ozone detectors are available from Dasibi, Glandale, Calif.

To produce the ozone-stressed yeast of the present invention, the yeast is grown in an environment that contains an effective amount of ozone. *Saccharomyces cerevisiae* is grown with aeration at 30° Celsius. An effective amount of ozone is an amount that is sufficient to cause a yeast response, yet is sub-lethal. By sub-lethal it is meant that at least 1% of the yeast survive after being exposed to ozone. Therefore, the amount of ozone applied to yeast should allow at least 1% to survive. However, the amount of ozone applied to the yeast may allow at least 10% of the yeast to survive the treatment. In another embodiment, the amount of ozone applied to the yeast should allow at least 50% of the yeast to survive the treatment. In a further embodiment, the amount of ozone applied to the yeast should allow at least 80% of the yeast to survive the treatment.

The ozone may be introduced to the yeast in any method effective to expose the yeast to the ozone. For example, the ozone may be introduced to the yeast through an aeration gas which includes the ozone and either air or oxygen. The aeration gas is usually at a temperature between about 15° Celsius and about 90° Celsius.

The yeast are exposed to a concentration of ozone for a time period sufficient to obtain a maximum amount of yeast that have produced cellular components effective against degradation of skin cell components. The yeast may be exposed to the ozone for several minutes to several days depending on yeast type, ozone concentration, aeration rates, temperature, and like. Typically the yeast is exposed to an ozone concentration between about 0.0001 millimole (mM) to about 1.0 mM for a period of 5 minutes to 72 hours. In another example, the yeast is exposed to an ozone concentration between about 0.01 mM and about 0.8 mM for a period of about 10 minutes to about 60 minutes. In another example, the yeast is exposed to a concentration of ozone between about 0.1 mM and about 0.5 mM for a period of from about 15 minutes to about 30 minutes.

Illustratively, when the yeast is exposed to ozone for a lengthier period of time it is suitable that the yeast is exposed to a lower concentration of ozone. Alternatively, when the yeast is exposed to ozone for a shorter period of time it is suitable that the yeast is exposed to a higher concentration of ozone. Without wanting to be bound by any theory, it is suggested that the ozone-stressed yeast respond to the presence of ozone by generating protective agents that counteract the detrimental effects of ozone.

The ozone-stressed yeast is then lysed to obtain ozone-stressed yeast lysate. The yeast can be lysed by a variety of methods known to one skilled in the art, including but not limited to, enzymes, high-speed agitation, changes in growth media, autolysis or changes in pH. The ozone-stressed yeast lysate typically contains water-soluble and water-insoluble components. The water-insoluble components may be separated from the water-soluble components.

The ozone-stressed yeast lysate may be filtered and purified to remove cellular bodies, odor and other undesirable materials. The ozone-stressed yeast lysate is tested to determine whether it is suitable for cosmetic use. Preferably two-dimensional polyacrylamide gel electrophoresis is performed, and the proteins present in the ozone-stressed yeast lysate are quantified.

Without wanting to be bound by any theory, it is suggested that the ozone-stressed yeast responds to the presence of the ozone by generating protective agents or cellular components, which are capable of counteracting the detrimental effects of ozone. It is possible to determine which proteins are produced by the ozone-stressed yeast by running a yeast gene microarray to determine which genes in the yeast are up-regulated or down-regulated as a result of the ozone treatment. The use of yeast gene microarrays allows comparison of changes that occur in yeast when different stresses, such as hydrogen peroxide, UV and ozone, are placed on the yeast. Gene microarrays are useful in demonstrating the differences these stresses can have on the proteins expressed by stimulating the growing yeast. *Saccharomyces cerevesiae* gene microarray chips are available from MWG Biotech (High Point, N.C.).

The ozone-stressed yeast lysates may be further purified by any number of means known to those skilled in the art including, but not limited to, chromatography, steam distillation, solvent extraction, centrifugation, decantation, filtration, or carbon treatment. The lysates of the present invention may be further concentrated by any means known to those skilled in the art including, but not limited to, evaporation, spray-drying, lyophilization, steam distillation or belt or drum drying.

The ozone-stressed yeast lysates may be used in personal care compositions. Such personal care compositions may provide skin cells with protection from ozone pollution or skin cell component degradation associated with exposure to ozone. Specifically, the addition of ozone-stressed yeast lysates may control the breakdown of vitamins C and E, DNA, RNA and bilayer lipids, which occurs in skin cells exposed to ozone. The personal care composition of the present invention may contain an effective amount of ozone-stressed yeast lysate and at least one preservative selected from the group consisting of alcohols, glycols, parabens, quaternary nitrogen-containing compounds, isothiazolinones, aldehyde-releasing agents, antioxidants and halogenated compounds. Illustrative alcohols include phenoxyethanol, isopropyl alcohol, and benzyl alcohol; illustrative glycols include propylene, butylene, and pentylene glycol; illustrative parabens (also known as parahydroxybenzoic acids) include methyl, propyl and butyl-parabens; illustrative quaternary nitrogen-containing compounds include, benzalkonium chloride, and Quatemium 15; illustrative isothiazolinones include methylisothiazolinone and methylchloroisothiazolinone; illustrative aldehyde-releasing agents include DMDM hydantoin, imidazolidinyl urea and diazolidinyl urea; illustrative antioxidants include butylated hydroxytoluen and tocopherol, and illustrative halogenated compounds include triclosan, and chlorhexidine digluconate. Examples of preservatives useful for the purposes of the present invention can be found, for example, in Steinberg, D. "Frequency of Use of Preservatives 2001" Cosmet. Toilet. 117, 41-44, (2002) and, "Preservative Encyclopedia" Cosmet. Toilet. 117, 80-96 (2002).

An effective amount of ozone-stressed yeast lysate is an amount of ozone-stressed yeast lysate that provides skin cells with adequate protection from exposure to ozone. Adequate protection may be provided by utilizing a concentration of ozone-stressed yeast lysate in a personal care composition that is sufficient to impart efficacy against ozone damage to at least a portion of the skin cells that are exposed to ozone present in the environment. The effective amount of the ozone-stressed yeast lysate is provided by incorporating the ozone-stressed yeast lysate into a personal care composition.

Preferably the amount of ozone-stressed yeast lysate is present in a personal care composition between 0.001% and 100% based on the weight of the personal care product. More preferably the ozone-stressed yeast lysate is present in the personal care composition in an amount between about 0.01% and about 50% based on the total weight of the personal care composition. Alternatively the ozone-stressed yeast lysate can be present in the personal care composition between about 1% and about 10% based on the total weight of the personal care composition.

Additionally, the personal care composition can optionally contain other functional ingredients such as, water, surfactants, emulsifiers, conditioners, emollients, waxes, oils, polymers, thickeners, fixatives, colorants, humectants, moisturizers, stabilizers, diluents, solvents, fragrances and the like, as well as active ingredients such as, for example, botanicals, neutraceuticals, cosmeceuticals, therapeutics, pharmaceutics, antifungals, antimicrobials, steroidal hormones, antidandruff agents, anti-acne components, sunscreens, preservatives and the like.

The ozone-stressed yeast lysate can be used in various types of cosmetic formulations including, but not limited to, lotions, ointments, creams, sprays, spritzes, aqueous or aqueous alcoholic mixtures, gels, mousses, patches, pads, masks, moistened cloths and wipes, solid sticks, clear sticks, lipsticks, aerosol creams, anhydrous powders, talcs, tonics, oils, emulsions, and bath salts. Such cosmetic formulations may be used as topical treatments for skin.

The ozone-stressed yeast lysates of the present invention may include the lysates alone or they may include the yeast lysates encapsulated in various chemical delivery vehicles known to those skilled in the art. Such cosmetically acceptable delivery vehicles include, but are not limited to, liposomes, niosomes, sub-micron emulsions, polymeric encapsulants, gels, creams, lotions, and combinations thereof.

The following Examples are intended to illustrate the art of the present invention and are not intended to limit the scope of the claims below.

EXAMPLES

Example 1

Example of Yeast Lysate from Grown *Saccharomyces*
Organism and Media

The organism used in this study was *S. cerevisiae* (Red Star baker's yeast). Stock culture was maintained on a yeast peptide dextrose (YPD) agar slant (Difco). The working culture was maintained in YPD broth at 4° C. The fermentation was carried out with the medium containing 10 270 g/L yeast extract, 8 g/L $NH_4SO_4$, 3 g/L $KH_2PO_4$, 2 g/L $MgSO_4$, and 0.5 mL/L Antifoam A. Unless otherwise stated, the working volume for fermentation was 2 liters (L).

Bioreactor

A New Brunswick Bioflo 110 benchtop bioreactor (Edison, N.J.) equipped with automatic 275 pH, temperature, agitation, dissolved oxygen (DO) and antifoam controls was used. The 2-L vessel was equipped with air in- and out-ports, alkali and medium addition ports, and effluent side ports. Medium pH was maintained at 5.5 by adding 4 M NaOH and/or 4 M H2SO4. Aeration was maintained at 1 vvm (volume of air/working volume of fermentor/min) and DO level was kept at 60% by cascading to the agitation. The fermentor was fed with 250 g/L of glucose solution at the rate of 1.2 mL/h.

Ozone

Ozone gas was produced from purified extra dry air by an ozone generator (Model Lab2B Ozonia, Elmwood Pk, N.J.). The inlet airflow rate was maintained at 0.5 L/min. The ozone generator was set to produce 0.5 g/h of ozone. The ozone-air stream from the ozone generator was mixed with 1.5 L/min of air. The mixture of ozone and air (0.5 part/1.5 part) was purged in to the fermentation medium. Ozone concentration was measured using indigo dye (see FIG. 1) and/or a UV spectroscopic method that indicates ozone at a frequency of 258 nm. All experimental work with ozone was done under a chemical hood. An activated carbon column absorbed excess ozone.

Stress Conditions

Cells of *S. cerevisiae* after 48 hours of fermentation ($1.0 \times 10^9$ cells/mL) were treated by ozone. The mixture of air and ozone (1.5 part/0.5 part) was purged through the fermentation broth for 15 minutes and 45 minutes (min). The cells were harvested before and after the treatment. The ozone concentration was kept around 0.01 mg/L (0.002 mM). The following samples of yeast lysate were: non-treated (A), 15 min (B), and 45 min (C).

Preparation of Yeast Lysate

Samples of *S. cerevisiae* for analytical tests were taken from fermentation broth after 48 hours at $1.0 \times 10^9$ cells/mL. Forty-five milliliters (mL) of culture sample were centrifuged (15000 rpm for 10 min) and washed with distilled water. The precipitate was resuspended in 45 mL of 10 mM phosphate buffer of pH 7, supplemented with phenylmethylsulphonyl fluoride (Sigma Chemical Co., St. Louis, Mo.) to 1 mM and pepstatin A (Sigma) to a concentration of 10 µM. Forty five mL glass beads (0.5 mm diameter; Biospec Products, USA) were added to the cell suspension. The suspension, in 90 mL container, was inserted into a Bead-beater (Biospec Products) and shaken at homogenization speed for 3 min. The sample chamber was cooled during the homogenization step by an ice bath. The protein concentration of samples was determined by BCA protein assay (Sigma). Samples of each lysate were analyzed as described below.

Effect of Ozone Stress on Yeast Protein Expression
Two Dimensional Polyacrylamide Gel Electrophoresis Two-dimensional electrophoresis was performed according to the method of O'Farrell (J. Biol. Chem. 250: 4007-4021, 1975) by Kendrick Labs, Inc. (Madison, Wis.) as follows: Isoelectric focusing was carried out in glass tubes of inner diameter 2.0 mm using pH 4-8 2.0% ampholines (Gallard Schlesinger Industries, Inc. Garden City, N.Y.) for 9600 volt-hrs. Fifty nanograms of an IEF internal standard, tropomycin, was added to each sample. Tropomycin shows two polypeptide spots of similar pI (ionic charge); the lower spot of MW 33,000 and pI 5.2 was marked with an arrow on the stained gels. The tube gel pH gradient plot for this set of ampholine was determined with a surface pH electrode.

After equilibration for 10 min in buffer "0" (10% glycerol, 50 mm dithiothreitol, 2.3% SDS and 0.062 M tris, pH 6.8), each tube gel was sealed to the top of a stacking gel that was on top of a 12% acrylamide slab gel (0.75 mm thick). SDS slab gel electrophoresis was carried out for hours at 12.5 mA/gel. The following proteins from Sigma were added as molecular weight standards to the agarose that sealed the tube gel to the slab gel: myosin (220,000), phosphorylase A (94,000), catalase (60,000), actin (43,000), carbonic anhydrase (29,000) and lysozyme (14,000). These standards appear along the basic edge of the silver-stained 12% acrylamide slab gel.

Limited Computerized Comparisons

Duplicate gels were obtained by the 2-D methodology as described above. One gel from each pair was scanned with a laser densitometer (Model PDSI, Molecular Dynamics Inc, Sunnyvale, Calif.). The scanner was checked for linearity prior to scanning with a calibrated Neutral Density Filter Set (Melles Griot, Irvine, Calif.). The images were analyzed using Progenesis Discovery software (version 2003.3, Nonlinear Technology) such that all major spots and all changing spots were outlined, quantified and matched on all the gels. The general method of computerized analysis for these pairs included automatic spot finding and quantification, automatic background subtraction (Progenesis algorithm) and automatic spot matching in conjunction with detailed manual checking of the spot finding and matching functions.

Results from computerized comparison are given in fold increase or decrease (difference) of the polypeptides for non-treated sample versus 15 min ozone-treated and non-treated versus 45 min ozone treated sample. The differences are calculated from spot percentages (individual spot density divided by total density of all measured spots). Increased (up-regulated) and decreased (down-regulated) polypeptide spots with a fold difference of ≥3 were taken into consideration.

For purposes of a two-dimensional gel electrophoresis, the term "up-regulated" implies that a protein has been over-expressed, while the term "down-regulated" implies that the protein has been under-expressed.

Summary of Tables

Table 1. Summary of proteins only present in non-treated yeast lysate and not present in yeast lysate treated for 15 minutes with ozone.

Table 2. Summary of proteins only present in 15 minute ozone treated yeast lysate and not present in non-treated yeast lysate.
Table 3. Summary of proteins up-regulated (i.e., present but increased) in 15 minute ozone-stressed yeast lysate but not increased in non-treated yeast lysate.
Table 4. Summary of proteins down-regulated (i.e., present but diminished) in 15 minute ozone-stressed yeast lysate but not diminished in non-treated yeast lysate.
Table 5. Summary of proteins only present in non-treated yeast lysate but not present in yeast lysate treated for 45 minutes with ozone.
Table 6. Summary of proteins only present in 45 minute ozone treated yeast lysate but not present 360 in non-treated yeast lysate.
Table 7. Summary of proteins up-regulated (i.e., present but increased) in 45 minute ozone-stressed yeast lysate but not increased in non-treated yeast lysate.
Table 8. Summary of proteins down-regulated (i.e., present but diminished) in 45 minute ozone-stressed yeast lysate but not diminished in non-treated yeast lysate.

TABLE 1

The table below indicates molecular weight (MW), pI (ionic charge) and spot number of proteins that were present only in non-treated samples. These proteins were not present in samples treated with 15 minutes of ozone. Therefore, four proteins, as shown in the table below, were eliminated due to 15 min of ozone treatment. (nd = not determined).

| Spot # | pI   | MW     |
|--------|------|--------|
| 574    | nd   | nd     |
| 575    | 5.41 | 21,245 |
| 576    | nd   | nd     |
| 577    | nd   | nd     |

TABLE 2

The table below indicates molecular weight, pI and spot number of proteins that were present only in samples exposed to 15 min of ozone treatment. These proteins were not present in non-treated samples. Therefore, the nine proteins as shown in the table below, were induced due to 15 min of ozone treatment. (nd = not determined)

| Spot # | pI   | MW     |
|--------|------|--------|
| 27     | 5.18 | 85,545 |
| 482    | 6.47 | 24,435 |
| 569    | nd   | nd     |
| 472    | 5.37 | 26,010 |
| 497    | 5.29 | 22,733 |
| 498    | 5.40 | 22,846 |
| 503    | 5.24 | 22,373 |
| 505    | 5.39 | 22,118 |
| 508    | 5.18 | 21,034 |

TABLE 3

The table below indicates molecular weight, pI and spot number of proteins that were increased in 15 min ozone treated samples. These proteins were not increased in non-treated samples. Therefore, six proteins, as shown in the table, were increased or up-regulated due to 15 min of ozone treatment.

| Spot # | pI   | MW     |
|--------|------|--------|
| 91     | 8.33 | 71,997 |
| 473    | 6.28 | 25,595 |
| 20     | 5.27 | 89,519 |

TABLE 3-continued

The table below indicates molecular weight, pI and spot number of proteins that were increased in 15 min ozone treated samples. These proteins were not increased in non-treated samples. Therefore, six proteins, as shown in the table, were increased or up-regulated due to 15 min of ozone treatment.

| Spot # | pI   | MW     |
|--------|------|--------|
| 132    | 5.66 | 61,063 |
| 424    | 6.38 | 30,699 |
| 507    | 5.55 | 21,755 |

TABLE 4

The table below indicates molecular weight, pI and spot number of proteins that decreased in 15 min ozone treated samples. These proteins did not decrease in non-treated samples. Therefore, two proteins, as shown in the table, were decreased or down-regulated due to 15 min of ozone treatment.

| Spot # | pI   | MW     |
|--------|------|--------|
| 535    | 6.71 | 18,224 |
| 562    | nd   | nd     |

TABLE 5

The table below indicates molecular weight, pI and spot number of proteins present only in non-treated samples versus 45 min ozone treated samples. Thirteen proteins had disappeared due to 45 min of ozone treatment. (nd = not determined).

| Spot # | pI   | MW     |
|--------|------|--------|
| 574    | nd   | nd     |
| 575    | 5.41 | 21,245 |
| 576    | nd   | nd     |
| 577    | nd   | nd     |
| 91     | 8.33 | 71,997 |
| 151    | 8.00 | 63,041 |
| 206    | 5.29 | 51,222 |
| 320    | 7.70 | 37,894 |
| 354    | 7.59 | 34,851 |
| 423    | 4.88 | 30,245 |
| 461    | 5.01 | 25,963 |
| 521    | 6.46 | 20,203 |
| 547    | 5.50 | 15,498 |

TABLE 6

The table below indicates molecular weight, pI and spot number of proteins that were present only in 45 min ozone treated samples. The proteins were not present in non-treated samples. Therefore, six proteins, as shown in the table, were induced due to 45 min of ozone treatment. (nd = not determined)

| Spot # | pI   | MW     |
|--------|------|--------|
| 27     | 5.18 | 85,545 |
| 482    | 6.47 | 24,435 |
| 569    | nd   | nd     |
| 580    | 8.13 | 50,971 |
| 581    | 7.71 | 36,880 |
| 582    | 6.89 | 33,351 |

TABLE 7

The table below indicates molecular weight, pI and spot number of proteins that increased in 45 min ozone treated samples. These proteins did not increase in non-treated samples. Therefore, seven proteins, as shown in the table, increased or were up-regulated due to 45 min of ozone treatment.

| Spot # | pI | MW |
|---|---|---|
| 424 | 6.38 | 30,699 |
| 507 | 5.55 | 21,755 |
| 384 | 7.34 | 32,405 |
| 387 | 4.77 | 32,635 |
| 451 | 7.77 | 26,152 |
| 458 | 7.67 | 26,019 |
| 481 | 7.04 | 24,181 |

TABLE 8

The table below indicates molecular weight, pI and spot number of proteins that decreased in 45 min ozone-treated samples. These proteins did not decrease in non-treated samples. Therefore, eight proteins, as shown in the table, decreased, or were down-regulated due to 45 min of ozone treatment.

| Spot # | pI | MW |
|---|---|---|
| 535 | 6.71 | 18,224 |
| 2 | 6.68 | 183,807 |
| 4 | 6.78 | 167,243 |
| 61 | 4.97 | 73,486 |
| 225 | 6.03 | 49,737 |
| 316 | 6.27 | 39,083 |
| 533 | 6.29 | 18,395 |
| 545 | 9.18 | 15,513 |

Example 2

Yeast Gene Microarray Analysis: Comparing Effects of Ozone Verses Hydrogen Peroxide on Gene Expression To determine whether ozone caused yeast to respond differently than it responds to hydrogen peroxide, yeast was exposed to either ozone or hydrogen peroxide for the same length of time. The yeast was then subjected to microarray analysis to determine what genes were up-regulated and which were down-regulated as a result of the treatments. The following test protocols were employed in this study.

Yeast Cell Culture and Treatment

Cell cultures of S. cerevisiae were grown as described in more detail above. At the desired time after treatment, a 3-6 ml aliquot of the yeast culture was obtained and the cell density was measured spectrophotometrically at 600 nm. Culture samples having an Optical Density (OD) between 1 and 2 and were diluted with culture media as necessary to bring them within this range and the final volume of the aliquot was recorded. The aliquot was then centrifuged to pellet the yeast cells. The supernatant was discarded after centrifugation. The pellet was resuspended in lysis buffer using a ratio of 100 µl lysis buffer per ml of original culture volume (volume recorded prior to centrifuging). An additional ~200 µl of 0.4-0.5 mm glass beads was added to assist the lysing procedure.

Because yeast cells are difficult to lyse it was necessary to monitor the process to make sure that the nucleic acids were being released. After briefly mixing the sample, an initial 2 µl aliquot was obtained and diluted with 1 ml of nuclease free water. This sample was read at 260 nm and served as a "baseline" measurement for free nucleic acids. The remaining untested sample was then vigorously vortexed at 1-minute intervals. After each interval, a 2 µl aliquot was prepared and read as described above. As the yeast cells were lysed, the absorbance of the aliquot at 260 nm increased and then leveled off as the lysis process was completed. Total lysing normally occurs within 2-5 rounds of vortexing. After completing the lysis process for each sample, the samples stored on dry ice (approximately −75° C.) until analysis was possible.

RNA Isolation (Ambion RNAqueous Kit)

An equal volume of 64% ethanol was added to a sample of the yeast cell lysates prepared as described above, and the tubes were vortexed. After combining all tubes into one container, up to 700 µl of the mixture was transferred to a glass fiber filter cartridge. The cartridge was loaded into a 1.5 ml collection tube and was centrifuged for 1 minute at 14,000 RPM. The flow-through was discarded and the remaining mixture was loaded into the filter cartridge and the centrifugation process was repeated until all of the mixture had been processed. The filter was then washed to remove any residual cellular debris from the RNA bound to the glass fibers applying 700 µl of wash solution 1 (1 time) and 500 µl of wash solution 2 (2 times) to the filter cartridge and centrifuging at 14,000 RPM for 1 minute to pass each wash through the cartridge. After each wash the flow through was discarded. After the final wash one final spin was performed without wash solution to remove any residual wash solution in the filter cartridge. The RNA bound to the glass fibers within the cartridge was then eluted by applying 30 µl of Tris-EDTA buffer (10 mM Tris-HCl, 1 mM EDTA, preheated to 70-80° C.) to the cartridge and centrifuging the cartridge in a new collection tube at 14,000 RPM for one minute. For samples prepared from cell lysates and small tissues the elution process was repeated with an additional 30 µl of preheated TE buffer. For samples prepared from larger tissues (i.e. full thickness tissues) the elution process was repeated two additional times. After the RNA was eluted its concentration was quantified using a Ribogreen assay and its quality was assessed via gel electrophoresis.

RNA Concentration Assay (Molecular Probes Ribogreen Assay, Eugene, Oreg.)

The Ribogreen reagent was provided as a stock solution in DMSO. Prior to use the reagent was diluted 2000 fold in TE buffer. The RNA assay requires 200 µl of diluted Ribogreen reagent per sample to be tested and 1 ml of the reagent for the standards. Once prepared the diluted reagent was stored protected from light. A series of RNA standards were prepared by diluting purified ribosomal RNA derived from E. coli to the following concentrations: 2 µg/ml, 1 µg/ml, ng/ml, 40 ng/ml and 0 ng/ml (blank). Prior to assaying, the RNA samples prepared above were diluted 1000 fold in TE buffer. For the RNA assay, 100 µl of the diluted samples or standards were transferred to the wells of a black 96-well plate. The samples and standards were assayed in duplicate. After the samples/standards were added to the plate 100 µl of the diluted Ribogreen assay reagent was added to the wells and the plate was gently mixed and allowed to incubate for 5-10 minutes protected from the light. After this incubation the plate was read with a fluorometer using an excitation wavelength of 500 nm and an emission wavelength of 525 nm.

RNA Gel Electrophoresis

A 1% RNA gel was prepared by adding 0.3 g agarose to 21.6 ml diethylpyrocarbonate (DEPC) treated water. The agarose was dissolved by boiling the water in a microwave oven. After the solution was cooled to approximately 55° C. 5.4 ml of formaldehyde and 3.0 ml 10×MOPS (0.2 M MOPS

[pH 7.0], 20 mM sodium acetate, 10 mM EDTA, made in DEPC H$_2$O and filter sterilized) was added. After mixing, the agarose gel was cast in the horizontal gel apparatus with the loading slots placed on the side of the gel closest to the negative terminal. The gel was allowed to set for at least 1 hour at room temperature. While the gel set, 175 ml of 1×MOPS was prepared by diluting the 10× stock. After the gel was set the comb was removed and the buffer chamber of the gel apparatus was filled with 150-175 ml 1×MOPS (enough buffer was added to cover the gel with approximately 3 mm of buffer). The cover was placed on the apparatus, the electrical leads were attached to the power source, and the empty gel was run at 40 550 V (4 V/cm) for 5-10 minutes. While the gel was running the RNA samples were prepared by transferring ~1 µg of each sample RNA to a 600 µl PCR tube. DEPC H$_2$O was used to bring the total volume of all the samples to a common level and then 1-3 volumes of a gel-loading buffer (i.e. 5% glycerol, 1 mM EDTA, 0.025% bromophenol blue, 0.025% xylene cyanol FF, 20% formaldehyde, 50% formamide, 10 µg/ml ethidium bromide) was added. The samples were denatured by placing them at 65-70° C. for 5-15 minutes and then placing them on ice to cool. The samples were carefully loaded into the lanes (each loading slot can hold 10-15 µl of sample, depending upon the thickness of the gel) and the gel was run at 40 V for 1-3 hours. At the end of the run the RNA was visualized by placing the gel on a UV transilluminator. An RNA sample was used for subsequent processing if both the 18S and 28S ribosomal bands were clearly visible and there was little or no staining below the 18S band.

mRNA Amplification (Ambion MessageAmp aRNA Kit)

First Strand cDNA Synthesis: To start the first strand synthesis, 5 µg of total RNA for each sample was added to 600 µl PCR tubes and the total volume of liquid in the tube was adjusted to 12 µl with DEPC H$_2$O. To each tube, 1 µl of T7 Oligo(dT) primer was added and the tube was incubated at 70±2° C. for 10 minutes to denature the RNA and then placed on ice to allow the primer to anneal to the poly A ends of the mRNA. After cooling 2 µl of 10×first strand buffer, 1 µl of RNAse inhibitor and 4 µl of dNTP Mix was added to each tube, and the tube was placed at 42° C. As soon as the tube was heated, 1 µl of Reverse Transcriptase was added and the tubes were returned to 42±2° C. for 2 hours. At the end of the two hours the tubes were briefly centrifuged to collect all of the fluid at the bottom of the tube and then placed on ice.

Second Strand Synthesis and cDNA Purification: For the synthesis of the second strand of cDNA the following items was added to the tubes above (in this order): 63 µl DEPC H$_2$O, 10 µl 10× second strand buffer, 4 µl dNTP mix, 2 µl DNA Polymerase and 1 µl of RNAse H. The tube was mixed and then incubated at 16±2° C. for 2 hours. Towards the end of the 2 hour incubation a sufficient quantity of DEPC H$_2$O was warmed to 50±2° C. and a cDNA purification filter cartridge was equilibrated with 50 µl of cDNA binding buffer (one cartridge per sample) for at least 5 minutes. After the samples were finished incubating 250 µl of cDNA binding buffer was added to each tube and thoroughly mixed. The contents of the PCR tube was transferred to the cDNA purification filter cartridge. The cartridge was placed in a collection tube and centrifuged at 10,000 RPM for 1 minute. The flow-through was discarded and 650 µl of cDNA wash solution was added to the cartridge. The cartridge was centrifuged again and the flow-through was discarded, and then centrifuged one last time to ensure that the wash buffer was completely emptied from the filter. The cDNA was eluted by applying 10 µl of preheated DEPC H$_2$O to the filter and centrifuging the filter in a new collection tube at 10,000 RPM for one minute. This elution was performed one additional time to give a total volume of 16-18 µl of cDNA solution.

In Vitro Transcription to Synthesize aRNA and aRNA Purification: The in vitro transcription began by adding the following to the cDNA solution: 4 µl each of T7 ATP solution, T7 CTP solution, T7 GTP solution, T7 UTP solution, 4 µl of 10×Reaction buffer, and 4 µl of T7 enzyme mix. The tube was mixed and then incubated at 37±2° C. for 6-14 hours. Towards the end of the incubation a sufficient volume of Elution Solution was warmed to 50-60° C. and an aRNA filter cartridge was equilibrated with 100 µl of aRNA binding buffer for at least 5 minutes. At the end of the incubation period, 350 µl of aRNA binding buffer was added to the sample tubes and thoroughly mixed. An additional 250 µl of absolute ethanol was added to each tube. The mixture was then transferred to an aRNA filter cartridge; the cartridge was inserted into a collection tube and centrifuged at 10,000 RPM for 1 minute. The flow-through was discarded and 650 µl of aRNA wash buffer was added to the cartridge followed by centrifuging at 10,000 RPM for one minute. After discarding the flow through the cartridge was spun one final time to remove all traces of the wash buffer. The cartridge was transferred to a new collection tube and 25 µl of prewarmed Elution Solution was added to the cartridge. The cartridge was incubate for 2 minutes at room temperature and then aRNA was eluted by centrifuging for 1 minute at 10,000 RPM. This elution was performed one additional time to give a total volume of 45-50 µl of aRNA solution. The final concentration of the aRNA was determined by the Ribogreen assay as described above. In addition, the quality of the aRNA was checked via gel electrophoresis as described above. An aRNA sample was used for subsequent processing if a broad band of RNA was observed.

Labeling of aRNA with Fluorescent Dyes (PerkinElmer ASAP RNA Labeling Kit) and Purification of Labeled aRNA Labeling: Two tubes were prepared for the labeling process, one for Cy3 labeling (green) and one for Cy5 labeling (red). To the Cy3 tube was added 2 µg of aRNA prepared from the untreated/control sample (please note, the actual color assignment for each sample is not important, however, for consistency Cy3 is typically used for the untreated sample) and enough DEPC H$_2$O was added to bring the total volume up to 4 µl. To the Cy5 tube was added 2 µg of aRNA prepared from the sample treated with the test material and enough DEPC H$_2$O was added to bring the total volume up to 4 µl. To both tubes was added 5 µl of ASAP labeling buffer and 1 µl of the specific dye for the tube (Cy3 or Cy5). The tubes were incubated for 15 minutes at 85±2° C. At the end of the 15 minutes the tubes were placed on ice to cool and then add 2.5 µl of ASAP stop solution was added to each tube. The proportions given here were enough for analyzing one microarray chip.

Purification: To purify the labeled aRNA, a microcon YM-30 filter column was inserted into a collection tube and filled with 400 µl of TE buffer. The Cy3 and Cy5 probes was combined (12.5 µl of each) and then added to the microcon filter and thoroughly mixed with the TE buffer. The filter was centrifuged at 12,000 RPM for 8 minutes and the flow through was discarded. The column was washed twice with 400 µl of TE buffer, discarding the flow though each time. After the final wash the filter column was inverted, and placed into a new collection tube and centrifuged at 12,000 RPM for 2 minutes to collect the probe (the probe was concentrated in a volume of 2-30 µl of residual TE buffer).

Microarray Hybridization and Washing (Yeast Microarray Chips)

For hybridization, 45 µl of 10× control target RNA was mixed with 160 µl of DEPC water and 9 µl of 25× Agilent Fragmentation Buffer. This mixture was incubated at 60° C. for approximately 30 minutes in a hybridization oven. At the end of the incubation 225 µl of Agilent Hybridization Buffer was added along with the fluorescent aRNA probes prepared above. The mixture was incubated at 70° C. for 5-10 minutes in a waterbath. During this incubation period, an Agilent SUREHYB hybridization chamber was prepared by inserting a glass gasket slide into the bottom half of the chamber. At the end of the incubation period, the hybridization mixture (approximately 450 µl) was applied to the glass gasket slide and a Yeast Microarray Chip (High Point, N.C.) was placed face down on top of this gasket such that the hybridization solution was sandwiched between the glass gasket slide and the microarray face of the chip. The top half of the chamber was then attached and the connecting thumbscrew tightened. After verifying that there was good bubble formation in the chamber, it was placed into the hybridization oven for approximately 17 hours (60° C. and rotating at 4 RPM). At the end of the hybridization period the microarray/glass gasket was removed from the SUREHYB chamber and placed in 50 ml of wash solution 1 (room temperature, 6×SSC, 0.005% Triton X-102). After the gasket had fallen away from the microarray, the array was transferred to 300 ml of fresh wash solution on a magnetic stir plate. The array was washed while the solution was mixed at medium speed for 10 minutes and then transferred to 300 ml of wash solution 2 (0.1×SSX, 0.005% Triton X-102, 4° C.) for 5 minutes. After the final wash the array was centrifuged at 500 RPM for 5 minutes to dry it.

Microarray Scanning and Analysis

The microarrays were scanned with an Axon GenePix 4100A Scanner with the scanning resolution set to 10 µm and analyzed with GenePix Pro software. During the initial scan the PMT gains for the scanner were adjusted such that the cy5/cy3 image count ratios were between 0.88 and 1.12.

Calculations

RNA Ribogreen Assay

To derive the standard curve for the Ribogreen assay, the relative fluorescent units versus the known RNA concentrations in µg/ml for the standards were plotted and subjected to regression analysis to establish the line that best fit these data points. Mean RFU values for the test materials and untreated samples was used to estimate the amount of RNA present in each sample.

Microarray Calculations

The level of gene expression was related to the fluorescence intensity of the probed gene marker on the microarray. Since it is possible to have differences in labeling efficiency when making the Cy3 and Cy5, probes it is typical to normalize the fluorescence measurements between the two respective dyes before looking at changes in gene expression. Fluorescence intensities for the microarrays were subjected to global normalization. The total fluorescent signal for both dyes was normalized with a correction factor that would make the ratio of total intensities for both dyes equal to one. After normalizing the fluorescence measurements then it was possible to look for changes in gene expression. Criteria for evaluating changes in gene expression vary from study to study however typically three criteria are required:
1. The ratio of Cy3/Cy5 (untreated/treated) fluorescence intensity is greater than 1.5 or less than 0.66. This relates to a change in gene expression of at least +/−30%
2. The fluorescence intensity of the gene marker is greater than the background intensity.
3. The gene feature is clearly marked specifically by the aRNA probes and is not due to non-specific fluorescence (i.e. SDS streaks will leave fluorescent trails).

The data in the first two criteria were filtered via computer analysis of the data. The last criterion requires a visual inspection of the array spot to confirm.

Results of Microarray Analysis Comparing Ozone Stress to Hydrogen Peroxide Stress Using the protocols outlined above, two sets of yeast cells were stressed using either ozone or hydrogen peroxide. One set of yeast cells was exposed to 0.002 millimole (0.01 mg/L) of ozone for approximately one hour, while another set of yeast cells was exposed to 0.002 millimole (0.01 mg/L) of hydrogen peroxide for approximately one hour. Analysis of the genes that were subsequently affected by the stress were compared against untreated controls to determine which genes were up-regulated and down-regulated using the criteria defined above.

For purposes of gene microarray analysis, the term "up-regulation" or "up-regulated" implies that the gene is over-expressing RNA. The term "down-regulation" or "down-regulated" implies RNA is being under-expressed.

Results of Ozone and Hydrogen Peroxide Stressing on Yeast Compared to Untreated Yeast Yeast that was treated with ozone showed up-regulation of 570 genes and down-regulation of 342 genes. Yeast that was treated with hydrogen peroxide showed up-regulation of 502 genes and down-regulation of 57 genes.

Comparison of Genes Up-Regulated and Down-Regulated in Ozone Verse Hydrogen Peroxide Stressed Yeast Of the entire yeast genome present on the microarray, 570 genes were up-regulated in ozone-stressed yeast with 148 (26%) of them being different than those up-regulated by hydrogen peroxide. Likewise, of the 502 genes up-regulated by hydrogen peroxide, 80 (15.0%) were different than those up-regulated for ozone stressed yeast.

Of the 342 genes down-regulated by ozone stressing yeast, 321 (93.8%) were not down-regulated by hydrogen peroxide stress. Likewise, of the 57 genes down-regulated by hydrogen peroxide stress, 36 (63%) were not down-regulated by ozone stress.

Of the genes observed in the microarray analysis, it was noted that GAPDH was up-regulated in the presence of ozone, while it was not affected by hydrogen peroxide consistent with the earlier published scientific studies discussed above.

Example 3

In Vitro Protective Effect of Ozone-Stressed Yeast Lysate on Carmine Dye Oxidation In-vitro studies were performed by the degradation of potassium indigotrisulfonic acid upon exposure to ozone (Wentworth Jr. et al. 2003). Samples of ozone-stressed (or ozone treated) yeast lysate, non-ozone-stressed treated yeast lysate, and distilled water were compared. Approximately 36 mL of indigo reagent was mixed with 100 mL of sample to give an absorbance of 0.5. The final concentrations of yeast lysate samples were around 2%. Samples were then purged with 1.5 L/min of ozone/air stream containing 10 mg/L of ozone for 10 minutes. Absorbance values for samples were measured at 600 nm at different time intervals. Ozone has the unique ability to cleave the double bond in indigo to give the colorless isatin sulfonic acid compound, see below.

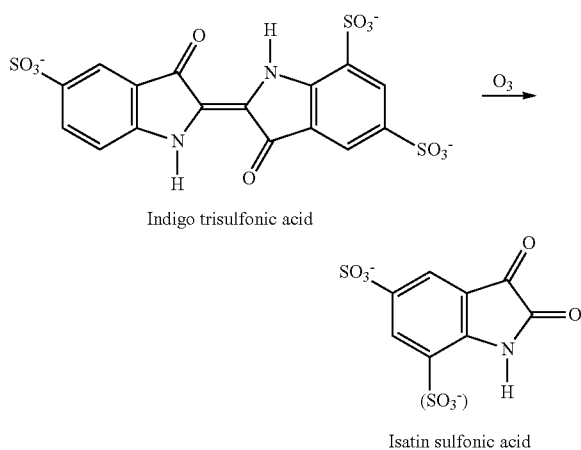

Indigo trisulfonic acid

Isatin sulfonic acid

Results from ozone exposure of water, non-ozone-stressed yeast lysate and ozone treated yeast lysate are shown in the photograph in FIG. 1. The ozone-stressed yeast lysate showed increased protection against the oxidizing power of ozone and less degradation to indigo potassium indigo trisulfonate compared to water and nontreated yeast lysate. This study suggests that ozone-stressed yeast lysate contains protective agents to retard the degradation of indigo dye. FIG. 1 shows the visual differences among the four samples. The first jar in the photograph, labeled "control", contains water and the indigo dye. The control jar does not contain yeast or yeast lysates and the solution in this jar was not subjected to ozone treatment. The second jar, labeled "water", contains water and the indigo dye. This jar also does not contain yeast or yeast lysate, however the solution in this jar was subjected to an ozone treatment to show how the ozone reacts with the indigo dye.

The third jar, labeled "ozone treated yeast", contains ozone-stressed yeast lysate in addition to water and the indigo dye. The solution in this jar was subjected to ozone treatment to show how the ozone reacts with the indigo dye in the presence of ozone-stressed yeast lysate.

The fourth jar, labeled "non-treated yeast", contains non-ozone-stressed yeast lysate in addition to water and the indigo dye. The solution in this jar was also subjected to ozone treatment to show how the ozone reacts with the indigo dye in the presence of non-ozone-stressed yeast lysate.

This test suggests several things, including: the indigo reagent is reactive to ozone; adding yeast lysate to the water and indigo dye solution provides some protection to the indigo dye from ozone degradation; and adding ozone-stressed yeast lysate to the water and indigo dye solution provides additional protection to the indigo dye from ozone degradation.

Example 4

Samples of the ozone-stressed yeast lysates were incorporated into a liposome comprising phospholipid and lecithin obtained from soybeans. The lysate was slurried together with the phospholipid and lecithin components and the mixture was homogenized using a high-pressure homogenizer obtained from Hydraulic Engineering Corporation (Brea, Calif.). The milky white mixture contained the ozone-stress yeast lysate encapsulated with the liposomal components.

Example 5

Samples of ozone-stressed yeast lysate were encapsulated in a maltodextrin and spray-dried to provide an essentially anhydrous powder of maltodextrin-encapsulated yeast lysate using the methodologies outlined in WO 2003/068161.

The following Proposed Examples illustrate skin care compositions according to the present invention that can be prepared using the ozone-stressed yeast lysate prepared using the method in Example 1.

Proposed Example

This example illustrates a high internal phase water-in-oil emulsion incorporating the ozone-stressed yeast lysate prepared as disclosed in Example 1.

| Ingredient | wt % |
| --- | --- |
| 1,3-dimethyl-2-imidazolidinone | 0.2 |
| polyoxyethylene (2) oleyl ether[1] | 5.0 |
| Bentone 38 | 0.5 |
| $MgSO_4 \cdot 7H_2O$ | 0.3 |
| Preservative[2] | 0.01 |
| Ozone-Stressed Yeast Lysate | 10.0 |
| Water | to 100 |

[1]For example, Brij 92 is polyoxyethylene (2) oleyl ether.
[2]Such as an aldehyde-releasing agent, for example DMDM Hydantoin.

Proposed Example

This example illustrates an oil-in-water cream incorporating the ozone-stressed yeast lysate prepared as disclosed in Example 1.

| Ingredient | wt % |
| --- | --- |
| Mineral Oil | 4 |
| 1,3-dimethyl-2-imidazolidinone | 1 |
| cetyl alcohol POE (10)[1] | 4 |
| cetyl alcohol[2] | 4 |
| Triethanolamine | 0.75 |
| Butane-1,3-diol | 3 |
| Xanthan gum | 0.3 |
| Methyl, Propyl and Butyl Paraben | 0.01 |
| Ozone-Stressed Yeast Lysate | 10.0 |
| Water | to 100 |

[1]For example, Brij 56 is cetyl alcohol POE (10)
[2]For example, Alfol 16RD is cetyl alcohol Proposed Example This example illustrates an alcoholic lotion incorporating a ozone-stressed yeast lysate prepared as disclosed in Example 1.

| Ingredient | wt % |
| --- | --- |
| 1,3-dimethyl-2-imidazolidinone | 0.3 |
| Ethanol | 40 |
| Ozone-Stressed Yeast Lysate | 10.0 |
| Water | to 100 |

Proposed Example

This example illustrates a sub-micron emulsion concentrate that contains a ozone-stressed yeast lysate prepared as described in Example 3.

| Ingredient | wt % |
| --- | --- |
| Trimethylolpropane Tricaprylate/Tricaprate | 18.0 |
| Glycerin | 8.0 |
| Cetearyl alcohol | 2.0 |
| Ceteareth 20 | 2.0 |
| Glyceryl stearate | 2.0 |
| BHT | 0.01 |
| Ozone-Stressed Yeast Lysate | 10.0 |
| Water | to 100 |

Proposed Example

| Ingredient | wt % |
| --- | --- |
| Water | 89 |
| Ozone-stressed yeast lysate | 10 |
| preservative (i.e. oxyethanol) | 1 |

What is claimed is:

1. A personal care composition comprising:
an ozone-stressed yeast lysate; and
a preservative,
wherein the preservative is selected from phenoxyethanol, isopropyl alcohol, benzyl alcohol, propylene glycol, butylene glycol, pentylene glycol, methylparaben, propylparaben, butylparaben, benzalkonium chloride, 1-(3-Chloroallyl)-3,5,7-triaza-1-azoniaadamantane chloride (QUATERNIUM 15), methylisothiazolinone, methylchloroisothiazolinone, 1,3-Bis(hydroxymethyl)-5,5-dimethylimidazolidine-2,4-dione (DMDM hydantoin), imidazolidinyl urea, diazolidinyl urea, butylated hydroxytoluene, tocopherol, triclosan, chlorohexidine digluconate, and combinations thereof,
wherein the ozone-stressed yeast lysate is produced by a method comprising the steps of:
  (a) exposing growing yeast to ozone by aerating the yeast for a time period of between five minutes and seventy-two hours with an aeration gas having an ozone concentration of from 0.0001 millimolar (mM) to 1.0 millimolar (mM) based on the total volume of the fermentation broth to produce ozone-stressed yeast;
  (b) lysing the ozone-stressed yeast to produce an ozone-stressed yeast lysate comprising water-soluble and water-insoluble components; and
  (c) separating the water-soluble components from the water-insoluble components to produce an ozone-stressed yeast lysate comprising the water-soluble components.

2. The personal care composition of claim 1, wherein the ozone-stressed yeast lysate is present in a concentration between 0.01% and 50% by weight based on the total weight of the personal care composition.

3. The personal care composition of claim 2, wherein the ozone-stressed yeast lysate is present in a concentration between 1% to 10% by weight based on the total weight of the personal care composition.

4. The personal care composition of claim 1, wherein the preservative is present in a concentration between 0.01% to 10% by weight based on the total weight of the personal care composition.

5. The personal care composition of claim 1, wherein the ozone-stressed yeast lysate is encapsulated with another component to provide a time-release characteristic to the ozone-stressed yeast lysate.

6. The personal care composition of claim 5, wherein the other component is selected from liposomes, niosomes, polymeric encapsulants, and combinations thereof.

7. The personal care composition of claim 1, wherein the ozone-stressed yeast lysate comprises at least one cellular component selected from cellular protein material, cellular nuclear material, cellular cytoplasmic material, cellular protoplasmic material, cell wall components, and combinations thereof.

8. The personal care composition according to claim 1, wherein the ozone-stressed yeast lysate is water-soluble.

9. The personal care composition according to claim 1, wherein the aeration gas has a temperature between 15° C. and 90° C.

10. The personal care composition according to claim 1, wherein the yeast is aerated for a time period between 10 minutes and 60 minutes with an aeration gas having an ozone concentration of from 0.01 mM to 0.8 mM.

11. The personal care composition according to claim 10, wherein the yeast is aerated for a time period between 15 minutes and 30 minutes with an aeration gas having an ozone concentration of from 0.1 mM to 0.5 mM.

12. The personal care composition according to claim 1, wherein the preservative is selected from phenoxyethanol, isopropyl alcohol, butylene glycol, pentylene glycol, propylparaben, butylparaben, benzalkonium chloride, 1-(3-Chloroallyl)-3,5,7-triaza-1-azoniaadamantane chloride (QUATERNIUM 15), methylisothiazolinone, methylchloroisothiazolinone, 1,3-Bis(hydroxymethyl)-5,5-dimethylimidazolidine-2,4-dione (DMDM hydantoin), diazolidinyl urea, triclosan, chlorohexidine digluconate, and combinations thereof.

13. The personal care composition according to claim 1, wherein the preservative is selected from the group consisting of phenoxyethanol, butylene glycol, propylparaben, butylparaben, and 1,3-Bis(hydroxymethyl)-5,5-dimethylimidazolidine-2,4-dione (DMDM hydantoin).

* * * * *